United States Patent [19]

Carr et al.

[11] 4,283,404
[45] Aug. 11, 1981

[54] AROYLETHENYL-PIPERIDINOBUTYROPHENONE ANTIPSYCHOTIC AGENTS

[75] Inventors: Albert A. Carr; Robert A. Farr, both of Cincinnati, Ohio

[73] Assignee: Richardson-Merrell Inc., Wilton, Conn.

[21] Appl. No.: 72,499

[22] Filed: Sep. 4, 1979

[51] Int. Cl.$^3$ ............... C07D 211/18; A61K 31/445
[52] U.S. Cl. ................................ 424/267; 542/438; 546/207; 546/215; 546/225
[58] Field of Search ............... 542/438; 546/207, 215, 546/225; 424/267

[56] References Cited

U.S. PATENT DOCUMENTS

| | | | |
|---|---|---|---|
| 3,080,372 | 3/1963 | Janssen | 546/226 |
| 3,484,446 | 12/1969 | Biel et al. | 548/207 |
| 3,580,910 | 5/1971 | Thiel et al. | 424/267 |
| 3,590,041 | 6/1971 | Kleeman et al. | 424/267 |
| 3,646,014 | 2/1972 | Bader et al. | 546/207 |
| 3,689,492 | 9/1972 | Schroeder et al. | 546/225 |
| 3,797,932 | 3/1974 | Yamamoto et al. | 424/267 |
| 3,816,443 | 6/1974 | Hernestam et al. | 424/267 |
| 3,852,455 | 12/1974 | Carr | 424/267 |
| 4,101,662 | 7/1978 | Ward et al. | 424/267 |

FOREIGN PATENT DOCUMENTS 516557  1/1972  Switzerland ..................... 542/438

OTHER PUBLICATIONS

Krauch et al., Organic Name Reactions, John Wiley & Sons, N.Y., N.Y., 1964, pp. 6–9.

Primary Examiner—Arthur P. Demers
Attorney, Agent, or Firm—John J. Kolano; Raymond A. McDonald; William J. Stein

[57] ABSTRACT

4-Aroylethnyl-1-piperidinobutyrophenone derivatives and pharmaceutically acceptable salts thereof of the following general structure:

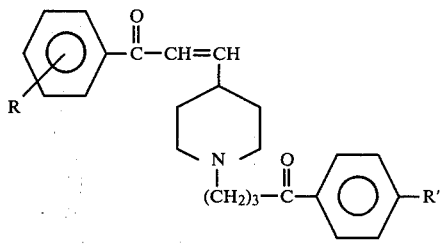

wherein R is hydrogen, alkyl, alkoxy, halogen or trifluoromethyl; and R' is hydrogen or halogen, are useful as antipsychotic agents. The novel compounds are produced by aldol condensation of an acetophenone with a protected 4-(4-formyl-1-piperidino)-butyrophenone.

12 Claims, No Drawings

AROYLETHENYLPIPERIDINOBUTYROPHENONE ANTIPSYCHOTIC AGENTS

BACKGROUND OF THE INVENTION

This invention relates to aroylethenylpiperidinobutyrophenone derivatives and pharmaceutically acceptable salts thereof which are useful as antipsychotic agents. More particularly, it relates to 4-aroylethenyl-1-piperidinobutyrophenones and to intermediates and processes for preparing the same.

Related 4-aroyl-1-piperidinobutyrophenones are known, for example, in U.S. Pat. Nos. 3,852,455, 3,888,867 and 4,101,662, Netherlands Patent No. 7,409,752, and Costall et al, *Psycopharmacologia,* 32(2), 161-170 (1973).

SUMMARY OF THE INVENTION

The 4-(β-aroylethenyl-1-piperidino)-butyrophenones of this invention have the general Formula I

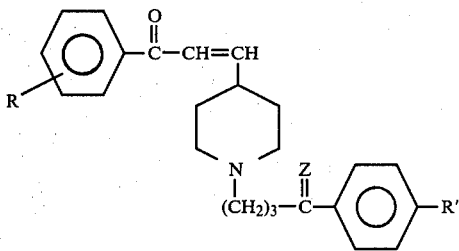

wherein Z is an oxygen atom; R is hydrogen, alkyl, alkoxy, halogen or trifluoromethyl; and R' is hydrogen or halogen. Pharmaceutically acceptable acid addition salts of the above compounds are also included within the scope of the invention as are pharmaceutical compositions comprising them and methods for preparing and using them.

The invention further includes compounds having the general Formulae I, II and III

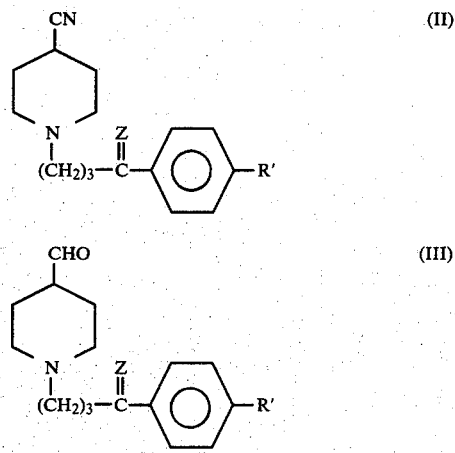

wherein R and R' are as defined for Formula I, and Z is a dialkyl or alkylene ketal function, which are key intermediates in the preparation of compounds of Formula I (Z=O).

DETAILED DESCRIPTION OF THE INVENTION

In the compounds of Formula I, the substituent R may be hydrogen, trifluoromethyl, alkyl, especially $C_{1-4}$ alkyl, such as methyl, ethyl, n-propyl, isopropyl, n-butyl, isobutyl, sec-butyl and tert-butyl, alkoxy, especially $C_{1-4}$ alkoxy, such as methoxy, ethoxy, n-propoxy, isopropoxy, n-butoxy, isobutoxy, sec-butoxy and tert-butoxy, or a halogen atom such as fluorine, chlorine or bromine. The R substituent may be in the ortho, meta or para position on the phenyl radical.

The substituent R' may be a hydrogen atom or a halogen atom such as fluorine, chlorine or bromine, especially fluorine.

The substituent Z is an oxygen atom or a dialkyl or alkylene ketal function, e.g., dialkoxy of 1-8, preferably 1-3 carbon atoms in each alkoxy group, e.g., methoxy or ethoxy, and alkylenedioxy of 2-8, preferably 2-4 carbon atoms, having 2 or 3 carbon atoms in the chain between the oxygen atoms, e.g., ethylenedioxy, 1,2-propylenedioxy and trimethylenedioxy.

The double bond linking the aroyl group and the piperidine ring may be cis or trans, or a mixture of geometric isomers. The compounds with a trans (E) double bond are preferred.

Especially preferred compounds of this invention are compounds of Formula I wherein Z is an oxygen atom; R is hydrogen, p-fluoro and p-chloro; and R' is a fluorine atom; and having a trans (E) double bond.

The invention also includes the pharmaceutically acceptable acid addition salts of the compounds of the hereinbefore set forth formulae, such as those salts with inorganic acids such as, for example, hydrochloric, hydrobromic, sulphuric, phosphoric acids and the like and with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic acid and the like.

Illustrative of compounds of this invention are, for example, 4-(4-benzoylethenyl-1-piperidino)-p-fluorobutyrophenone, 4-(4-p-fluorobenzoylethenyl-1-piperidino)-p-fluorobutyrophenone and 4-(4-chlorobenzoylethenyl-1-piperidino)-p-fluorobutyrophenone, especially the trans (E) isomers thereof.

The compounds of Formula I (Z=O) and their acid addition salts are antipsychotic agents. They can be administered in the form of pharmaceutical preparations in unit dosages suitable for oral or parenteral administration. The pharmaceutical preparations may be administered in solid form, for example, capsules, pills, or tablets, or in liquid form, either form optionally containing, in addition to the active compounds, a significant quantity of a pharmaceutically acceptable carrier. The compounds may be administered to animals, including rats, mice, dogs, cats, horses, pigs, cows, sheep, birds, warm-blooded animals and mammals, and humans. The quantity of the active compound of Formula I (Z=O) in the unit dosage can vary over a wide range, for example, to provide about 0.01-20 mg/kg of body weight of the treated subject per dose to achieve the desired effect. The effect can be obtained, for example, by consumption of from one to three 1-50 mg tablets taken 1-4 times daily.

The compounds of this invention can be used in the management of manifestations of psychotic disorders and can thus be used in a manner similar to haloperidol, a known antipsychotic agent.

Their effectiveness as antipsychotic agents is indicated by significant blocking of amphetamine grouped toxicity with low liability from extrapyramidal side effects, using standard test conditions.

The following reaction scheme illustrates a method of preparing compounds according to the invention:

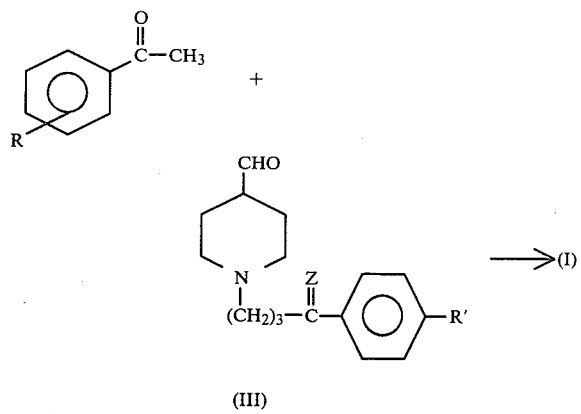

wherein R, R' and Z as ketal are as defined hereinbefore. The aldol condensation reaction between an acetophenone and a 4-formyl-1-piperidinobutyrophenone ketal is normally carried out in the presence of a mild base, such as piperidinium acetate, in a suitable solvent. The reaction is generally effected over the course of about four hours to about three days, advantageously at an elevated temperature such as the boiling point of the solvent. Suitable solvents include hydrocarbons, such as benzene and toluene. The cooled reaction mixture is partitioned between an organic and aqueous phase, and the crude ketal of Formula I (Z=ketal) is recovered from the organic phase after removal of the solvents.

Hydrolysis of the ketal is normally effected by stirring at 0°–40° C. in a mixture of water and an organic solvent such as tetrahydrofuran (THF), dioxane, dimethoxyethane (DME), or lower (e.g., $C_{1-4}$) alcohols, in the presence of a strong acid such as perchloric acid. Neutralization and extraction into an organic phase, washing with water and brine, drying over magnesium sulfate, and concentration yields a crude product of Formula I (Z=O). Further purification is typically effected by chromatography followed by formation of a salt, such as the hydrochloride, and recrystallization.

The novel 4-formyl-1-piperidinobutyrophenone ketal intermediates III as well as their 4-cyano precursors II may be prepared as follows:

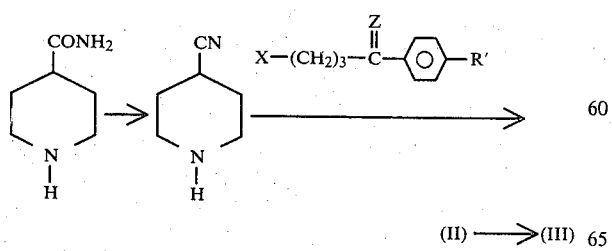

wherein R' and Z (ketal) are as defined hereinbefore and X is a reactive halogen such as bromine, chlorine or iodine, or an equivalent reactive leaving group. Commercially available piperidine-4-carboxamide is converted to 4-cyano piperidine, typically by reaction with trifluoroacetic anhydride, followed by hydrolysis of the resultant 4-cyano-1-trifluoroacetylpiperidine. Alkylation with a 4-halobutyrophenone ketal, typically the ethylenedioxy derivative, is normally carried out in the presence of an acid acceptor, such as, for example, sodium or potassium carbonate or bicarbonate, and is optionally catalyzed by a small amount of potassium iodide, in a suitable solvent. The reaction is generally effected over the course of about four hours to about three days, advantageously at an elevated temperature such as the boiling point of the solvent. Suitable solvents include aromatic hydrocarbons, such as toluene, xylene or chlorobenzene, ketones such as methyl isobutyl ketone, or lower alcohols such as ethanol, propanol, butanol and the like. Preferably, the reaction is run using potassium carbonate in n-butanol at reflux for five hours. The cooled reaction mixture is partitioned between an organic and aqueous phase and the product ketal II isolated from the organic phase after removal of solvents. The cyano group is reduced to an aldehyde function using a hydride reducing agent, advantageously diisobutylaluminum hydride, typically in a hydrocarbon solvent such as hexane or benzene. The normally exothermic reaction is advantageously conducted at room temperature, and the quenched product mixture partitioned between an organic and aqueous phase. Evaporation of the organic solvent leaves a crude imine which is hydrolyzed to the aldehyde, typically by treatment with a weak acid such as tartaric acid in an aqueous solvent such as aqueous THF at 0° C. for 0.5 to 2 hours. Partition of the product between an organic and aqueous phase, and isolation of the organic phase after removal of solvents, gives the formyl ketal III, suitable for use in the subsequent aldol condensation of SCHEME 1.

Preparation of the 4-halobutyrophenone ketals used in the reaction of SCHEME 2 is effected by reacting an appropriate glycol in benzene or toluene with a commercially available 4-halobutyrophenone, catalyzed by p-toluenesulfonic acid (HOTs) with azeotropic water removal, typically by use of a Dean-Stark trap. Reaction time varies from 12 to 72 hours, generally 40–48 hours.

EXAMPLES

The following examples are illustrative of the invention.

EXAMPLE 1

4-(4-Cyano-1-piperidino)-p-fluorobutyrophenone ethylene ketal (II, R'=F, Z=OCH$_2$CH$_2$O)

4-cyanopiperidine is prepared by reacting 130 g (1.02 moles) of piperidine-4-carboxamide (Aldrich Chemical Company) and 454 g (2.16 moles) of trifluoroacetic anhydride, and heating at reflux for 19 hours. Trifluoroacetic anhydride and trifluoroacetic acid are removed in vacuo, and the residual 4-cyano-1-trifluoroacetylpiperidine is added slowly to 345 g (2.5 moles) of potassium carbonate in 650 ml water and 1500 ml methanol. The reaction mixture is heated until most of the methanol boils off, 500 ml of benzene is added and the solution is heated until the vapor reaches a temperature of 85° C. The cooled reaction mixture is saturated with NaCl, extracted with methylene chloride, and the extracts dried over sodium sulfate and concentrated. The residue is dissolved in ether, filtered, concentrated in vacuo and distilled to give 30.2 g of 4-cyanopiperidine, b.p. 115°–116° C. at aspirator pressure.

A mixture of 11.1 g (0.10 mole) of 4-cyanopiperidine, 24.8 g (0.10 mole) of the ethylene ketal of 4-chloro-p-fluorobenzophenone (prepared by ketalizing the ketone with ethylene glycol in benzene/HOTs using a Dean-Stark trap) and 21 g (0.152 mole) of potassium carbonate in 200 ml of n-butanol are refluxed for 17 hours. Water is added to the cooled reaction mixture, the aqueous layer saturated with NaCl and the organic layer diluted with ether. The aqueous layer is extracted with benzene and the combined organic layers dried over magnesium sulfate and concentrated to give 31.5 g of the ethylene ketal of 4-(4-cyano-1-piperidino)-p-fluorobutyrophenone as a pale yellow oil. The isolated product is suitable for use in the reduction reaction of EXAMPLE 2.

EXAMPLE 2

4-(4-Formyl-1-piperidino)-p-fluorobutyrophenone ethylene ketal (III, R′=F, Z=OCH$_2$CH$_2$O)

To a solution of 6.4 g (20 mmoles) of the cyano-ketal of EXAMPLE 1, in 80 ml of toluene, under an argon atmosphere, is added a solution of 24.5 ml (23 mmoles) of 0.94 M diisobutyl aluminum hydride in hexane, resulting in an exothermic reaction. After stirring at 25° C. for 2 hours, quenching with methanol, and partitioning the resulting mixture between ether and aqueous alkali, the organic layer is washed with water, brine, dried over magnesium sulfate and concentrated in vacuo to give a crude imine. The imine is dissolved in 75 ml of THF, to which is added 0.36 ml (20 mmoles) of water, the solution cooled to 0° C., and 3.0 g (20 mmoles) of DL-tartaric acid is added. Only sufficient additional water is added to form a clear solution. After stirring at 0° C. for 20 minutes, and quenching with sodium bicarbonate, the mixture is poured into water, extracted twice with ether, the ether extracts washed with brine, dried over magnesium sulfate and concentrated in vacuo to give the desired aldehyde III, suitable for use in the subsequent aldol condensation reaction.

EXAMPLE 3

(E)-4-(4-Benzoylethenyl-1-piperidino)-p-fluorobutyrophenone (I, Z=O, R=H, R′=F) (hydrochloride salt)

A mixture of 8.1 g (25 mmoles) of the aldehyde-ketal produced in EXAMPLE 2 and 3.24 ml (28 mmoles) of acetophenone in 65 ml benzene containing 2.53 ml (26 mmoles) piperidine and 1.42 ml (25 mmoles) glacial acetic acid, is heated at reflux for 24 hours in an apparatus fitted with a Dean-Stark trap for separation of water. The cooled reaction mixture is concentrated in vacuo and the resultant ketal IV is hydrolyzed by addition of 15 ml of 70% perchloric acid and 25 ml of water to a solution of the ketal in 125 ml THF and 60 ml water, and stirring at room temperature for 21 hours. The hydrolysis mixture is poured into 450 ml of cold dilute alkali and 125 ml toluene, the organic layer separated and the aqueous layer extracted twice with ether/toluene. The combined organic extracts are washed with water, brine, dried over magnesium sulfate and concentrated in vacuo to give 13.8 g of crude product as an oil. The oil is chromatographed on silica gel, dissolved in ethanol and converted to the hydrochloride salt, which is recrystallized from butanone/methanol, m.p. 211° C. (dec.).

EXAMPLE 4

(E)-4-(4-p-Fluorobenzoylethenyl-1-piperidino)-p-fluorobutyrophenone (I, Z=O, R=p-F, R′=F) (hydrochloride salt)

By the procedure described in EXAMPLE 3, and using p-fluoroacetophenone, the desired hydrochloride salt is obtained. Recrystallization from butanone/benzene gives the pure product, m.p. 173.5°–175° C.

EXAMPLE 5

(E)-4-(4-p-Chlorobenzoylethenyl-1-piperidino)-p-fluorobutyrophenone (I, Z=O, R=p-Cl, R′=F) (hydrochloride salt)

By the procedure described in EXAMPLE 3, using p-chloroacetophenone, the desired hydrochloride salt is obtained. Recrystallization from butanone/methanol gives the pure product, m.p. 172.5°–173.5° C.

EXAMPLE 6

Tablet Formulation

Exemplary of a representative tablet formulation of an active compound of this invention, there may be mentioned the following:

|  | Per Tablet |
| --- | --- |
| (a) 4-(4-p-fluorobenzoylethenyl-1-piperidino)-p-fluorobutyrophenone hydrochloride | 25.0 mg |
| (b) Wheat starch | 3.5 mg |
| (c) Lactose | 10.0 mg |
| (d) Magnesium stearate | 0.5 mg |

A granulation obtained upon mixing lactose with a portion of the starch and granulated starch paste made from the remainder of the starch is dried, screened and mixed with the active ingredient (a) and the magnesium stearate. The mixture is compressed into tablets weighing 39.0 mg each.

We claim:

1. A compound of the formula

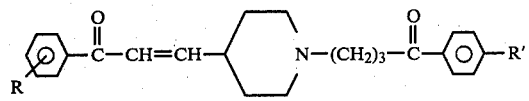

wherein R is hydrogen, C$_{1-4}$ alkyl, C$_{1-4}$ alkoxy, fluorine, chlorine, bromine, or trifluoromethyl; and R′ is hydrogen, fluorine, chlorine or bromine; and pharmaceutically acceptable acid addition salts thereof.

2. A compound of claim 1, wherein R′ is fluorine.

3. The compound of claim 1, which is 4-(4-benzoylethenyl-1-piperidino)-p-fluorobutyrophenone, and pharmaceutically acceptable acid addition salts thereof.

4. The compound of claim 1, which is 4-(4-p-fluorobenzoylethenyl-1-piperidino)-p-fluorobutyrophenone, and pharmaceutically acceptable acid addition salts thereof.

5. The compound of claim 1, which is 4-(4-p-chlorobenzoylethenyl-1-piperidino)-p-fluorobutyrophenone, and pharmaceutically acceptable acid addition salts thereof.

6. A compound of claim 1, having the formula

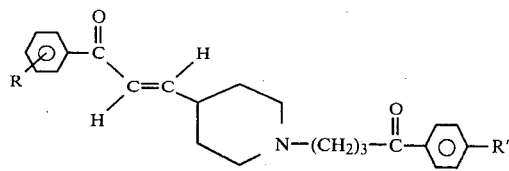

wherein R and R' are as defined therein; and pharmaceutically acceptable acid addition salts thereof.

7. The compound of claim 6, which is (E)-4-(4-benzoylethenyl-1-piperidino)-p-fluorobutyrophenone, and pharmaceutically acceptable acid addition salts thereof.

8. The compound of claim 6, which is (E)-4-(4-p-fluorobenzoylethenyl-1-piperidino)-p-fluorobutyrophenone, and pharmaceutically acceptable acid addition salts thereof.

9. The compound of claim 6, which is (E)-4-(4-p-chlorobenzoylethenyl-1-piperidino)-p-fluorobutyrophenone, and pharmaceutically acceptable acid addition salts thereof.

10. A pharmaceutical composition comprising in unit dosage form from about 1 mg to 50 mg of a compound of the formula

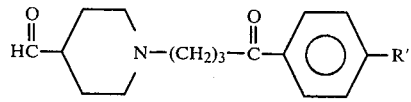

wherein R is hydrogen, $C_{1-4}$ alkyl, $C_{1-4}$ alkoxy, fluorine, chlorine, bromine or trifluoromethyl; and R' is hydrogen, fluorine, chlorine or bromine; and a significant amount of a pharmaceutically acceptable carrier.

11. A compound of the formula

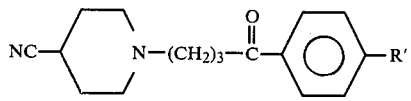

wherein R' is hydrogen, fluorine, chlorine or bromine; and Z is selected from dialkoxy of 1–8 carbon atoms in each alkoxy group and alkylenedioxy of 2–8 carbon atoms and 2–3 carbon atoms in the chain.

12. A compound of the formula wherein R' is hydrogen, fluorine, chlorine or bromine; and Z is selected from dialkoxy of 1–8 carbon atoms in each alkoxy group and alkylenedioxy of 2–8 carbon atoms and 2–3 carbon atoms in the chain.

* * * * *